US 6,643,006 B1

(12) United States Patent
Hsu et al.

(10) Patent No.: US 6,643,006 B1
(45) Date of Patent: Nov. 4, 2003

(54) METHOD AND SYSTEM FOR REVIEWING A SEMICONDUCTOR WAFER USING AT LEAST ONE DEFECT SAMPLING CONDITION

(75) Inventors: Chin-Jung Hsu, North Andover, MA (US); Arnold Cheng, North Chelmsford, MA (US); Xin Song, Waltham, MA (US)

(73) Assignee: Inspex, Inc., Billerica, MA (US)

( * ) Notice: Subject to any disclaimer, the term of this patent is extended or adjusted under 35 U.S.C. 154(b) by 0 days.

(21) Appl. No.: 10/016,996

(22) Filed: Dec. 13, 2001

(51) Int. Cl.[7] .............................................. G01N 21/00
(52) U.S. Cl. ................ 356/237.2; 356/394; 356/237.4; 356/237.5
(58) Field of Search .......................... 356/237.1–237.6, 356/394; 364/468.16, 468.17, 468.28, 552, 490; 382/8, 26, 145, 149, 240, 318; 702/181, 117

(56) References Cited

U.S. PATENT DOCUMENTS

| | | | | |
|---|---|---|---|---|
| 5,161,202 A | * | 11/1992 | Kitakado et al. ............... 382/8 |
| 5,539,752 A | * | 7/1996 | Berezin et al. ............. 364/490 |
| 5,761,064 A | * | 6/1998 | La et al. ................. 364/468.17 |
| 5,896,294 A | * | 4/1999 | Chow et al. ............ 364/468.28 |
| 5,982,921 A | * | 11/1999 | Alumot et al. ............... 382/145 |
| 6,028,664 A | * | 2/2000 | Cheng et al. ............. 356/237.4 |
| 6,466,895 B1 | * | 10/2002 | Harvey et al. .............. 702/181 |

* cited by examiner

Primary Examiner—Frank G. Font
Assistant Examiner—Sang H. Nguyen
(74) Attorney, Agent, or Firm—Kriggsman & Kriegsman (57) ABSTRACT

A data management system for reviewing at least one layer of at least one semiconductor wafer is connected to a first inspection device and a second inspection device. The system includes a server which is connected to the first and second inspection devices. A review station is connected to the server. In use, the first inspection device scans at least one layer of at least one semiconductor wafer so as to yield a first set of detected defects. In addition, the second inspection device scans at least one layer of at least one semiconductor wafer so as to yield a second set of detected defects. The first and second sets of detected defects are uploaded into a database in the server. The review station is then used to extract a sample of the first and second sets of detected defects from the database using at least one defect sampling condition.

28 Claims, 6 Drawing Sheets

METHOD AND SYSTEM FOR REVIEWING A SEMICONDUCTOR WAFER USING AT LEAST ONE DEFECT SAMPLING CONDITION

BACKGROUND OF THE INVENTION

The present invention relates generally to the review of a semiconductor wafer for defects and more particularly to a novel method and system for reviewing a semiconductor wafer for defects at a review station using at least one defect sampling condition.

Integrated circuits (ICs) are commonly manufactured through a series of processing steps. Very often more than a hundred processing steps are performed to produce a properly functioning integrated circuit chip.

A semiconductor material, commonly in the shape of a wafer, serves as the substrate for integrated circuits. Semiconductor ICs are typically manufactured as an assembly of a hundred or more chips on a single semiconductor wafer which is then cut up to produce the individual IC chips. Typically, a wafer made of silicon is used as the integrated circuit substrate, the silicon wafer being approximately 150–300 mm in diameter and 0.6–1 mm thick. During the manufacturing process, the silicon wafer is first polished and cleaned to remove all contaminant particles situated thereon. The silicon wafer is then treated in preparation for a series of processing steps involving a plurality of photolithographic patterns (also commonly referred to as masks). In the production of integrated circuits, microelectronic circuits are formed onto the silicon wafer through a process of layering. In the layering process, conductive and insulative layers of thin films are deposited and patterned onto the silicon wafer. Each layer is patterned by a mask designed specifically for it, the mask defining the areas within the wafer that are to be treated such as by etching or implanting.

Semiconductor fabrication technology today deals with silicon wafers which are approximately 200 mm in diameter and which feature geometries with dimensions well below 0.5 $\mu$m (micrometer). Due to the high complexity and level of integration of integrated circuits, the absence of contaminants on every layer of the wafer is critical in order to realize acceptable levels of product yield. Specifically, the presence of one contaminant particle larger than the half the width of a conductive line on the silicon wafer can result in the complete failure of a semiconductor chip produced from the wafer. Such a chip has to be discarded which thereby decreases the percentage yield per wafer and increases the overall cost of the individual wafers. Therefore, a critical task facing semiconductor process engineers is to identify and, as soon as possible, to eliminate sources of surface contamination on each layer of a semiconductor wafer.

Accordingly, inspection systems are well known in the art and are commonly used to detect, identify and correct yield limiting defects which are introduced onto the surface of a semiconductor wafer during the fabrication process of integrated circuits.

It is well known in the art for a plurality of inspection systems to be used to inspect a semiconductor wafer at various points in time during the fabrication of said semiconductor wafer. As such, each inspection system serves to inspect the semiconductor wafer after the treatment of a particular layer of the integrated circuit. By using multiple inspection instruments to scan various layers of the semiconductor wafer for contaminant particles, the user is able to discern where, and more specifically on which layer, a defect first occurred in the manufacturing process. The ability to discern where a defect first occurred is extremely useful in removing the defect and in preventing future contamination.

However, in order to properly ascertain where in the manufacturing process a defect first occurred, it is necessary to compare all of the defects detected by each inspection system. Accordingly, it is well known in the art to connect to all of the inspection systems used to scan a semiconductor wafer to a data management system server.

One or more data analysis stations are also often connected to the data management system server. Each of the data analysis stations enables the user to perform a series of cursory analysis tests (e.g., trend charts) of the defect data detected by the inspection devices. Although useful, data analysis stations are not capable of determining the class of a particular defect (i.e., what the defect is).

Accordingly, one or more review stations are often connected to the data management system server. A review station is typically in the form of a high magnitude optical microscope which enables the user to closely examine individual defects which are detected by the one or more inspection systems. Specifically, the microscope enables the operator to determine the particular class (i.e., the nature) of each defect.

Typically, a review station receives all of the defect data compiled by a particular inspection system for one particular layer of one particular wafer. The operator is then required to thoroughly examine each individual defect using the optical microscope.

Although well known and widely used in the art, the particular exchange of defect data between the review station and the data management system server as described above suffers a notable drawback. Specifically, the review station receives from the data management system server only those defects which are detected by a particular inspection system for a particular layer of a particular wafer. As a result, the operator is precluded from examining common types of defects which may be present on different layers of the same wafer. As such, the inability of the operator to compare the defect data of multiple layers of wafers renders more difficult the ability to determine when during the fabrication process of a semiconductor wafer recurrent contaminant particles are introduced, which is highly undesirable.

Accordingly, it is known in the art for software to be installed onto the data management system server which creates a central database into which all of the raw historic defect data compiled by the one or more inspection systems are uploaded. In this manner, the operator is able to extract from the database all of the defect data which was detected by a particular inspection system (which is selected by the operator) at a particular point in time (which is selected by the operator), thereby providing the operator with the ability to access any defect which has been detected by the one or more inspection systems, which is highly desirable.

Although useful and well known in the art, the software described above suffers from a notable drawback. Specifically, the operator is required to extract from the database the entire set of defect data which was detected by the selected inspection system at the selected point in time. As a result of the operator's inability to filter out different types of defect data, a considerably large number of defects are often extracted from the database and are sent to the review station for further examination. In this situation, the operator is required to closely examine each of the relatively large number of defects which are sent to the review station, which is considerably time consuming and labor intensive, which is highly undesirable.

SUMMARY OF THE INVENTION

It is an object of the present invention to provide a method and system which includes at least one inspection device for inspecting the one or more semiconductor wafers for defects.

It is another object of the present invention to provide a method and system as described above which includes a data management system server connected to said at least one inspection device, said data management system server storing the raw historic defect data detected by said at least one inspection device.

It is yet another object of the present invention to provide a method and system as described above which includes at least one review station for examining under high magnification individual defects which are stored in said data management system server.

It is still another object of the present invention to provide a method and system as described above in which said review station is able to extract one or more defects which are stored in said data management system server.

Accordingly, there is a system for reviewing at least one layer of at least one semiconductor wafer for defects, said system being interfaced to a first inspection device which scans the at least one layer of the at least one semiconductor wafer for defects, said first inspection device producing a first set of detected defects from scanning the at least one layer of the at least one semiconductor wafer, said system being interfaced to a review station for reviewing the at least one layer of the least one semiconductor wafer, said system comprising a server connected to said first inspection device and said review station, said server comprising a database into which said first set of detected defects is stored, and review client software which interfaces which said review station, said review client software enabling a sample of said first set of detected defects to be extracted from the database using at least one defect sampling condition.

There is also provided a method for inspecting at least one layer of at least one semiconductor wafer for defects using at least one inspection mechanism, said at least one inspection mechanism being connected to a server which includes a database, said server being connected to a review station, said method comprising the steps of scanning the at least one layer of the at least one semiconductor wafer using said at least one first inspection mechanism, said scanning step yielding a first set of detected defects, storing said first set of detected defects into said database, requesting a sample of said first set of detected defects using at least one defect sampling condition, said requesting step being performed at said review station, extracting the sample of said first set of detected defects using at least one defect sampling condition from the database, said extracting step being performed by said server in response to said requesting step, and sending the extracted sample of said first set of detected defects from said server to said review station.

Various other features and advantages will appear from the description to follow. In the description, reference is made to the accompanying drawings which form a part thereof, and in which is shown by way of illustration, a specific embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
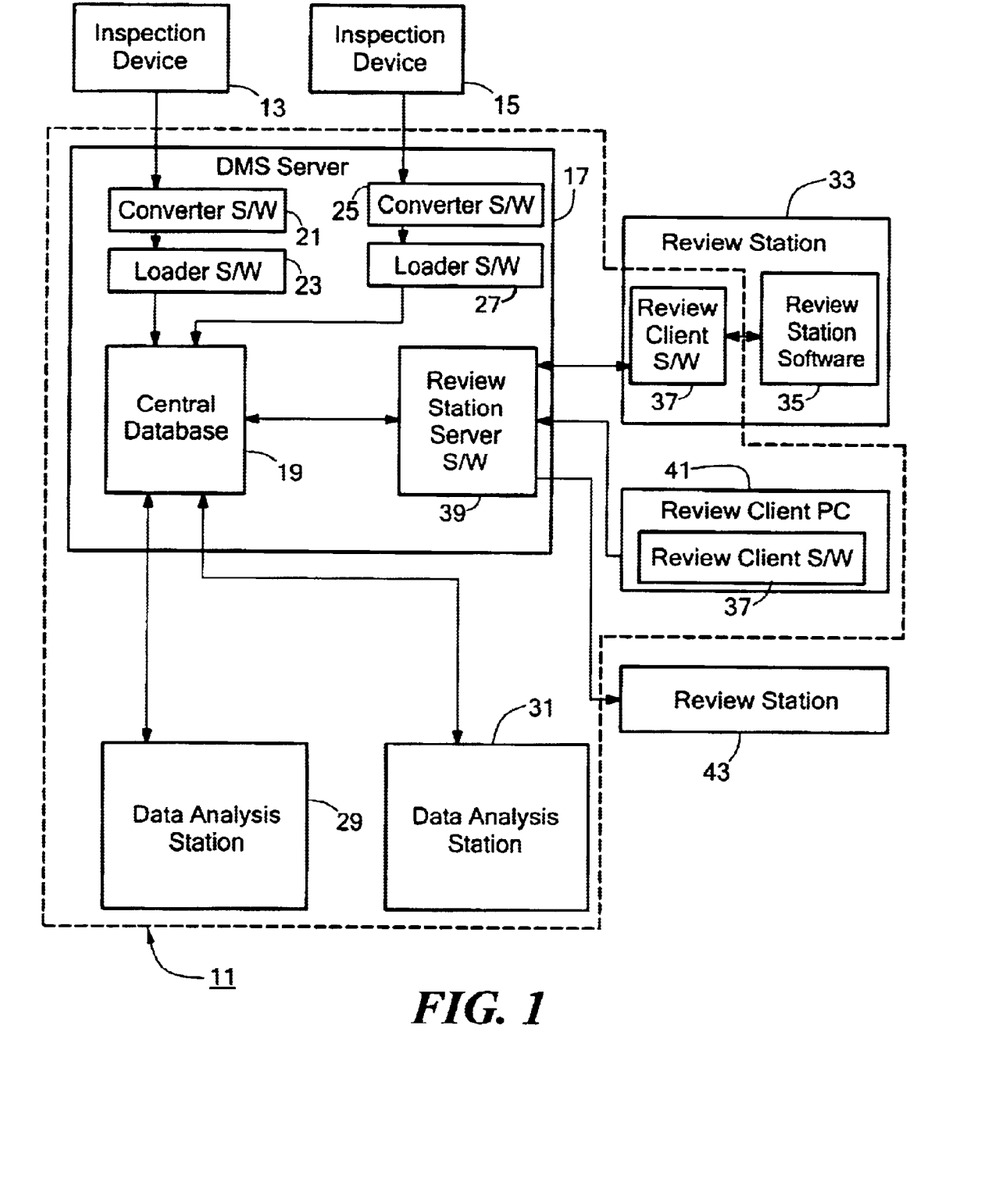
FIG. 1 is a block diagram of a data management system for reviewing at least one layer of at least one semiconductor wafer for defects, said system being constructed according to the teachings of the present invention.

Referring now to FIG. 1, there is shown a block diagram of a data management system (DMS) for reviewing at least one layer of at least one semiconductor wafer for defects. The data management system is constructed according to the teachings of the present invention and is identified generally by reference numeral 11.

Data management system (DMS) 11 is connected to a first inspection device 13 and a second inspection device 15. Inspection devices 13 and 15 represent conventional inspection systems which are used to scan the surface of a semiconductor wafer for defects, such as scratches, contaminant particles and/or other similar imperfections.

Specifically, inspection devices 13 and 15 preferably represent conventional inspection devices which comprise a light source, such as a laser, and a light sensitive imaging camera. In use, the light source is used to scan the surface of the semiconductor wafer by means of illuminating particular regions of the surface of the wafer. The light sensitive imaging camera is positioned relative to the wafer to pick up scattered light. The imaging camera creates a visual based on the number of photons which disperse from the wafer as the laser performs its scanning function. The camera will detect light scattered from any defects situated on the wafer, the intensity of the scattered light being generally proportional to the size of the defects, wherein the larger defects generally reflect more photons onto the imaging camera than the smaller defects.

Inspection devices 13 and 15 are used to detect various defects which are present on the one or more layers of the one or more semiconductor wafers. Specifically, inspection devices 13 and 15 are used to determine general information concerning the nature of the defects which are present on the one or more wafers (e.g., the location of said defects on the wafer, the size of said defects on the wafer and the density of said defects on the wafer). However, it should be noted that magnified examination of each of said defects is required in order to determine the particular classification of each of said defects (i.e., what the defect is) and is accomplished by a review station, typically using a high magnification microscope, as will be described further in detail below.

Inspection devices 13 and 15 are preferably disposed to scan for defects on the surface of each semiconductor wafer at different stages during the fabrication process of said wafer. In this manner, inspection devices 13 and 15 can be used to determine the particular point in time during the fabrication process when said defects were introduced onto the surface of the wafer, which is highly useful in preventing the contamination of future wafers.

It should be noted that data management system (DMS) 11 is not limited to having a pair of inspection devices 13 and 15 be connected thereto. Rather, it is to be understood that additional inspection devices could be connected to data management system (DMS) 11 to scan a semiconductor wafer at different stages during the fabrication of said wafer without departing from the spirit of the present invention.

Data management system (DMS) 11 comprises a data management server 17, server 17 being connected to inspection devices 13 and 15. Data management server 17 is preferably a UNIX®-based server, such as a Hewlett-Packard® server. As will be described further in detail below, the entire historical set of defects which are detected by inspection devices 13 and 15 is uploaded into data management server 17.

Data management server 17 includes a central database 19 into which the entire historical set of defects which are detected by devices 13 and 15 is stored. Preferably, central database 19 runs on Oracle® version 7.0 or later versions.

A first piece of conversion software 21 is installed onto server 17. Similarly, a first piece of loading software 23 is installed onto server 17. As can be appreciated, conversion software 21 and loading software 23 are installed onto server 17 in such a manner so that the entire historical set of defects detected by inspection device 13 is first normalized, or translated, by conversion software 21 from its native file format to a server-friendly, central database file format. The normalized data is then loaded into database 19 by loading software 23.

Similarly, a second piece of conversion software 25 and a second piece of loading software are installed onto server 17. As can be appreciated, conversion software 25 and loading software 27 are installed onto server 17 in such a manner so that the entire historical set of defects detected by inspection device 15 is first normalized, or translated, by conversion software 25 from its native file format to a server-friendly, central database file format. The normalized data is then loaded into database 19 by loading software 27.

In this manner, all of the defects detected by inspection devices 13 and 15 on the various layers of the various semiconductor wafers are stored within central database 19 of data management system (DMS) 11. As a result, the user is capable of extracting any particular detected defect which is stored within database 19 for further examination, as will be described further in detail below.

It should be noted that, because all of the defects detected by both inspection devices 13 and 15 are stored within a single central database 19, the user is able to extract the defects which are present on a particular layer of a particular wafer, which is highly desirable. Specifically, because central database 19 includes detected defects at various stages during the fabrication process of a particular wafer, the defects added onto the wafer during the deposition of a particular layer (commonly referred to in the art simply as adder defects) can be determined by taking the total defects present on the wafer at a particular fabrication station and eliminating all the defects which were present on the wafer at the previous fabrication station.

A first data analysis station 29 is connected to central database 19 of server 17. Similarly, a second data analysis station 31 is connected to central database 19 of server 17. Data analysis stations 29 and 31 are preferably in the form of conventional Windows®-based personal computers which are connected to server 17 through a local area network (LAN) cable or other similar communication medium.

Data analysis stations 29 and 31 are capable of extracting the raw defect data stored in database 19 in order to perform data analysis functions (e.g., trend charts) of said raw defect data. Although system 11 is shown comprising two data analysis stations, it is to be understood that system 11 could comprise fewer or more data analysis stations without departing from the spirit of the present invention.

A review station 33 is connected to DMS server 17 through a local area network (LAN) cable or other similar communication medium. Review station 33 enables the user to closely inspect individual defects which are stored in central database 19 in order to precisely determine the classification, or nature, of said defects (i.e., to determine whether each defect is a scratch, a contaminant particle, a pit, a bump or other similar imperfection).

Review station 33 is preferably in the form of a conventional, high magnification, inspection microscope which is manually operable. As an example, review station 33 may be in the form of an optical microscope (OM). As another example, review station 33 may be in the form of a scanning electron microscope (SEM). As another example, review station 33 may be in the form of a focused ion beam (FIB) microscope.

Review station software 35 on review station 33 enables the user to manually review individual defects at high levels of magnification. Preferably, review station software 35 includes a series of graphical user interfaces (GUI) to facilitate the process of reviewing individual defects at high levels of magnification.

Review client software 37 is also loaded onto review station 33, review client software 37 enabling review station 33 to interface with database 19 via review station server software 39. Review client software 37 is preferably in the form of standalone software that can run on either a Windows® NT® or UNIX® operating system, review client software 37 being designed to run on review station 33 using the series of graphical user interfaces (GUI).

Review station server software 39 is loaded onto server 17. Together, review station server software 39 and review client software 37 allow for the direct uploading, downloading, conversion and transfer of data between database 19 of server 17 and review station 33 in several different file formats, which is highly desirable.

Review client software 37 enables the user to request specific defect data stored in central database 19. Specifically, review station server software 39 responds to the request from the review station 33 and extracts the requested defect data from database 19. Review station server software 39 then converts the extracted defect data from a database file format to a native file format and then exports said file to review station 33. The defect data contained in the exported file is accessible through the graphical user interfaces (GUI) of review station 33.

It should be noted that data management system (DMS) 11 is not limited to having a single review station be connected thereto. Rather, additional review stations could be connected to system 11 without departing from the spirit of the present invention.

It should also be noted that review client software 37 need not be directly installed onto the review station. To the contrary, review client software 37 could alternatively be installed onto a review client personal computer (PC) 41, review client PC 41 being connected to server 17. In addition, a review station 43 separate from review client PC 41 could be connected to server 17. As such, in the same manner as mentioned in the previous paragraphs, particular defect data which is requested by review client PC 41, is extracted from database 19 and is exported onto review station 43 for further examination.

It should be noted that review client software 37 is provided with defect sampling capabilities, which is a principal feature of the present invention. Specifically, review client software 37 allows for the user to extract particular types of defect data directly from central database 19 using one or more defect sampling conditions. As will be described further in detail below, said one or more defect sampling conditions relate to the specific characteristics of the defects stored in central database 19.

The particular defect sampling conditions limit, or filter, the number and type of defect data which are extracted from central database 19 and which are exported onto review station 33 for further review. As a result, the user is able to limit his/her examination to those particular defects with which he/she is most concerned, thereby decreasing the overall examination time, which is highly desirable in a wafer manufacturing facility.

The particular process for extracting defect data from database 19 using one or more defect sampling conditions includes two principal steps: (1) establishing one or more defect sample plans, each defect sample plan including one or more defect sampling conditions, during a defect sample plan set-up step, and (2) performing the run-time operation step of requesting defect data from database 19 using one of the defect sample plans established in the previous step.

Figure 3:
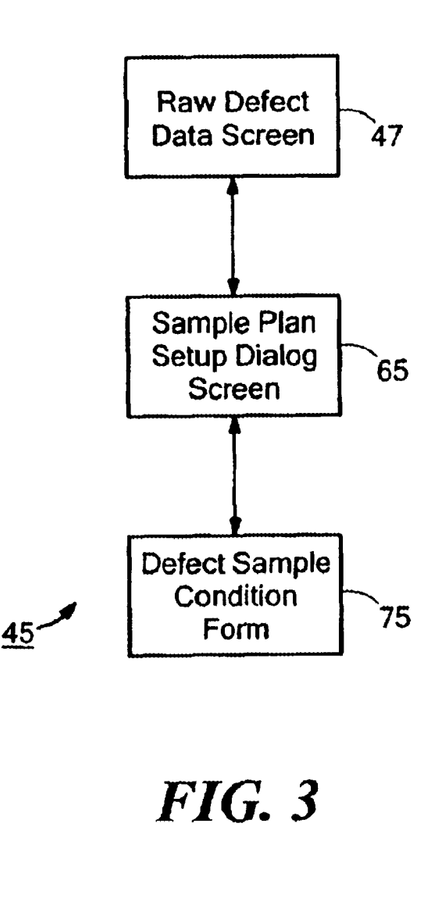
FIG. 3 is a partial flow chart detailing a sequence of graphical user interfaces for performing the defect sample plan set-up step shown in FIG. 2.

Referring now to FIG. 3, there is shown a flow chart detailing the sequence of graphical user interfaces (GUI) which are provided on review station 33 by review client software 37 to enable the user to perform the defect sample plan set-up step noted above, the series of graphical user interfaces being identified generally by reference numeral 45. It should be noted that system 11 is preferably constructed so that only authorized personnel can change, edit or set-up the desired defect sample plans.

The first graphical user interface provided is a raw defect data screen which lists all of the defect data which has been uploaded into central database 19 from inspection devices 13 and 15, said first interface being represented by reference numeral 47 in FIG. 3.

Figure 5:
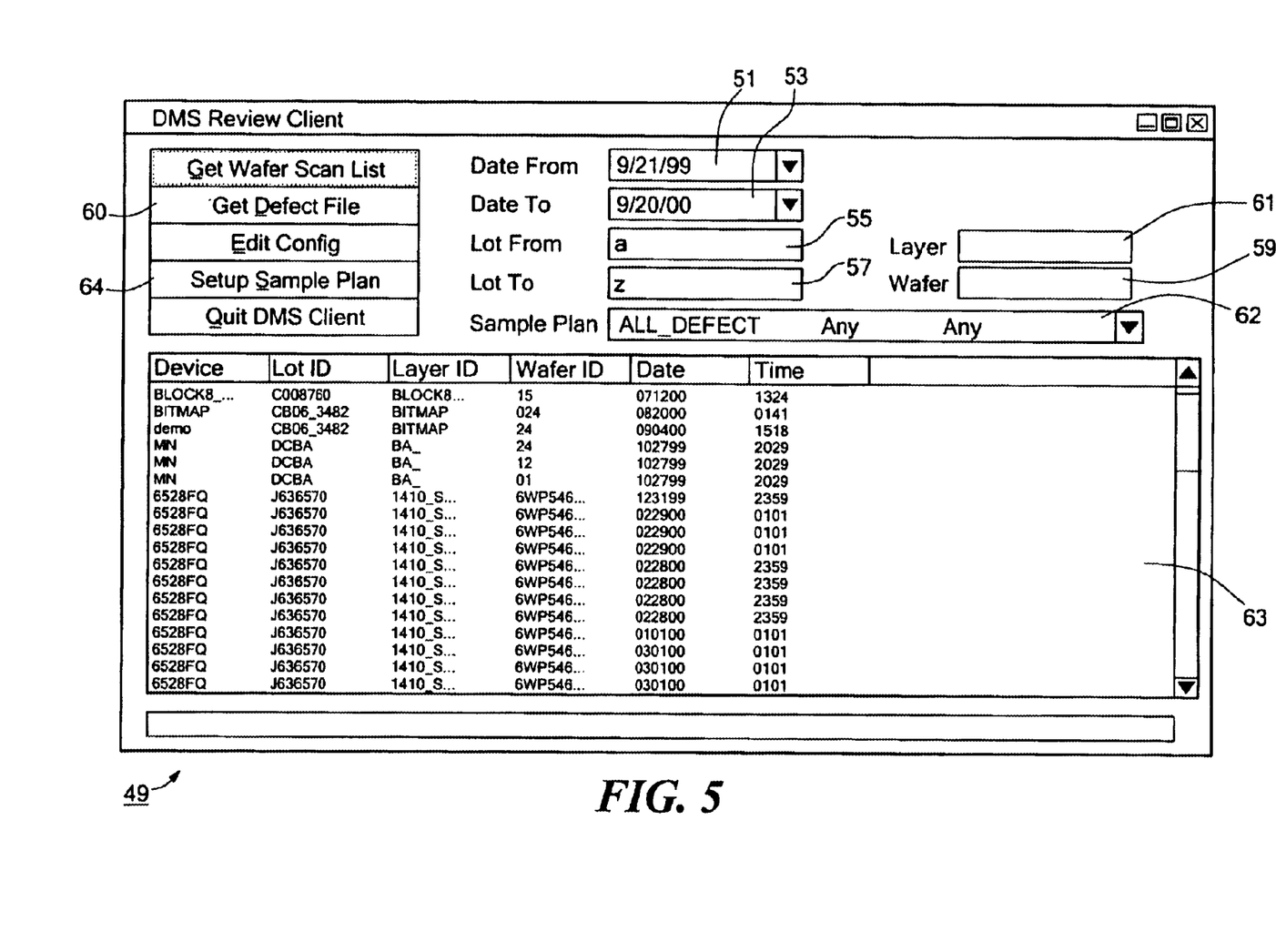
FIG. 5 is a representative screen showing the raw defect data graphical user interface of FIG. 3.

A representative screen of first graphical user interface 47 is shown in FIG. 5, said screen being identified generally by reference numeral 49. As shown in FIG. 5, screen 49 provides the user with the ability to filter out some of the raw historical defect data which is to be displayed thereon. Specifically, screen 49 includes a plurality of windows for filtering out some of the particular defect data which is to be extracted from central database 19.

As an example, screen 49 enables the user to extract defect data from central database 19 which was detected within a particular time period. Specifically, screen 49 includes a "Date From" window, as represented by reference numeral 51 in FIG. 5, as well as a "Date To" window, as represented by reference numeral 53 in FIG. 5, to condition that the extracted defect data fall within a specific detected time period. As another example, screen 49 enables the user extract defect data from central database 19 which was detected on a particular lot of semiconductor wafers (wherein one lot equals 25 semiconductor wafers). Specifically, screen 49 includes a "Lot From" window, as represented by reference numeral 55 in FIG. 5, and a "Lot To" window, as represented by reference numeral 57 in FIG. 5, to condition that the extracted defect data be limited to a particular lot of wafers.

As another example, screen 49 enables the user to extract defect data from central database 19 which was detected on a particular wafer. Specifically, screen 49 includes a "Wafer" window, as represented by reference numeral 59 in FIG. 5, to condition that the extracted defect data be limited to a particular wafer.

As another example, screen 49 enables the user to extract defect data from central database 19 which was detected on a particular layer of the one or more wafers scanned by inspection devices 13 and 15. Specifically, screen 49 includes a "Layer" window, as represented by reference numeral 61 in FIG. 5, to condition that the extracted defect data be limited to a particular layer of each wafer.

As another example, screen 49 enables the user to extract defect data from central database 19 using a particular defect sample plan (which includes one or more defect sampling conditions). Specifically, screen 49 includes a "Sample Plan" window, as represented by reference numeral 62 in FIG. 5, which enables the user to select a particular defect sample plan to utilize during the run-time operation of extracting defect data from central database 19. The function of "Sample Plan" window 62 will be described further in detail below in conjunction with the run-time operation of extracting defect data from central database 19.

In addition to including various defect sampling limitations windows, screen 49 includes a large defect data window, as represented by reference numeral 63 in FIG. 5, which displays the extracted defect data. Large defect data window 63 includes severable user configurable columns (e.g., lot, wafer, layer, date, time, tech, device, inspect, defect count, and fab) to arrange and identify the complete list of extracted data.

Having pulled up first graphical user interface 47, the user is then required to click on a "Setup Sample Plan" button, which is represented by reference numeral 64 in FIG. 5, to continue defect sample plan set-up process 45. Clicking on "Setup Sample Plan" button 64 pulls up the second graphical user interface, said second graphical user interface being represented by reference numeral 65 in FIG. 3. Second graphical user interface 65 is a sample plan setup dialog screen which lists all of the defect sampling conditions which are to be implemented in each defect sample plan in order to reduce the amount of defect data which is to be extracted from central database 19 and exported into review station 33.

Figure 6:
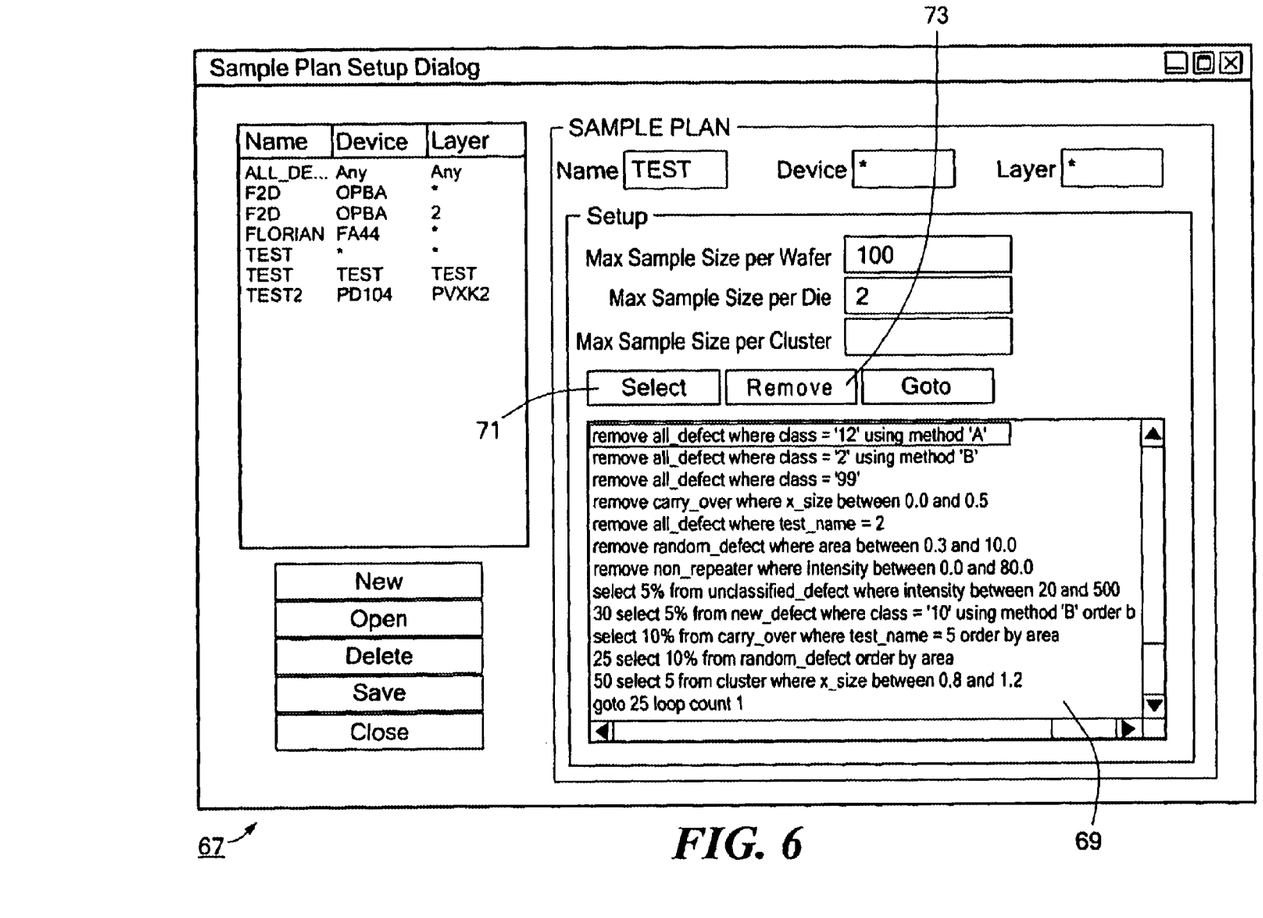
FIG. 6 is a representative screen showing the sample plan setup dialog graphical user interface of FIG. 3.

A representative screen of second graphical user interface 65 is shown in FIG. 6, said screen being identified generally by reference numeral 67. As shown in FIG. 6, screen 67 provides the user with the ability to introduce one or more defect sampling conditions into each defect sample plan in order to reduce the amount of defect data to be extracted from central database 19 and to be exported into review station 33, which is highly desirable. Each of the defect sampling conditions relates to a particular characteristic of a defect.

Screen 67 is provided with a primary window 69 which displays all of the defect sampling conditions which are to be implemented for a defect sample plan during the extraction of defect data from central database 19. To add a particular defect sampling condition to primary window 69, screen 67 is provided with a "Select" button 71 and a "Remove" button 73. "Select" button 71 enables the user to select what type of defect data is to be extracted from database 19. "Remove" button 73 enables the user to select what type of defect data is not to be extracted from database 19.

As can be appreciated, clicking on "Select" button 71 or "Remove" button 73 pulls up the third graphical user interface, said third graphical user interface being represented by reference numeral 75 in FIG. 3. Third graphical user interface 65 is a defect sample condition form which can be used to add a particular defect sampling condition to a defect sample plan, said defect sampling condition filtering the types of defect data to be extracted from central database 19 and exported into review station 33.

Figure 7:
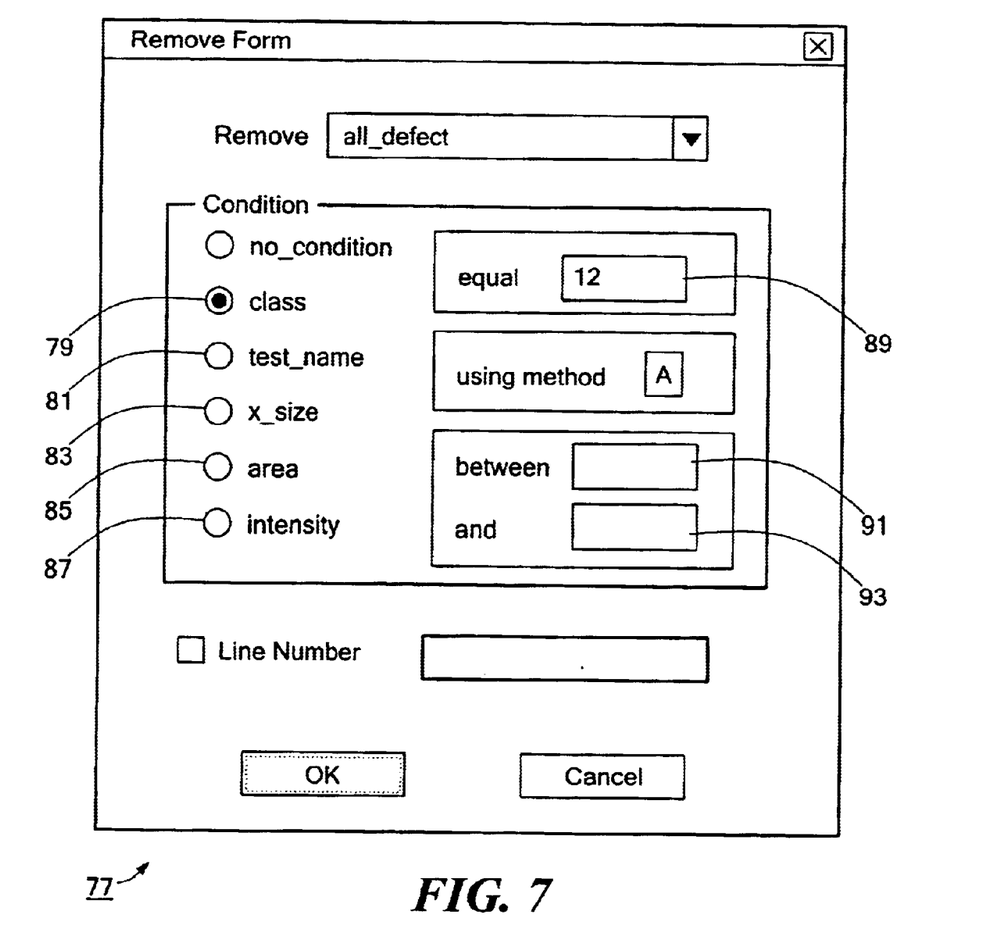
FIG. 7 is a representative screen showing the select/ remove form graphical user interface of FIG. 3.

A representative screen of third graphical user interface 75 is shown in FIG. 7, said screen being identified generally by reference numeral 77. It should be noted that screen 77 displays a form for removing particular defects. However, it is to be understood that screen 77 could be altered slightly to serve as a form for selecting particular defects without departing from the spirit of the present invention.

Screen 77 is provided with a plurality of different defect sampling conditions which may be selected, each defect sampling condition relating to a particular characteristic of each defect. Specifically, screen 77 includes a defect class condition, as represented by reference numeral 79 in FIG. 7, which relates to the particular classification type of each defect. Screen 77 also includes a defect test name condition, as represented by reference numeral 81 in FIG. 7, which relates to the particular test name of each defect. Screen 77 further includes a defect size condition, as represented by reference numeral 83 in FIG. 7, which relates to the particular size of each defect. Screen 77 also includes a defect density condition, as represented by reference numeral 85 in FIG. 7, which relates to the particular density of a cluster of defects. Screen 77 further includes a defect intensity condition, as represented by reference numeral 87 in FIG. 7 which relates to the particular intensity of each defect.

In addition to the particular defect sampling conditions, screen 77 is provided with windows for introducing the exact value limitation, as represented by reference numeral 89 in FIG. 7, or the range of value limitations, as represented by reference numerals 91 and 93 in FIG. 7, to be used in conjunction with the particular defect sampling condition selected.

Upon completion of implementing the particular defect sampling condition on third graphical user interface 75, the user is returned to second graphical user interface 65. With second graphical user interface 65 pulled up, if the user is satisfied with the list of defect sampling conditions displayed in window 69, the user can return to first graphical user interface 47, thereby completing defect sample plan set-up process 45.

Having set-up the various defect sampling conditions for each defect sample plan in process 45, the user is able to perform the run-time operation of extracting a defect data sample from database 19 using one of the defect sample plans established through process 45.

Figure 4:
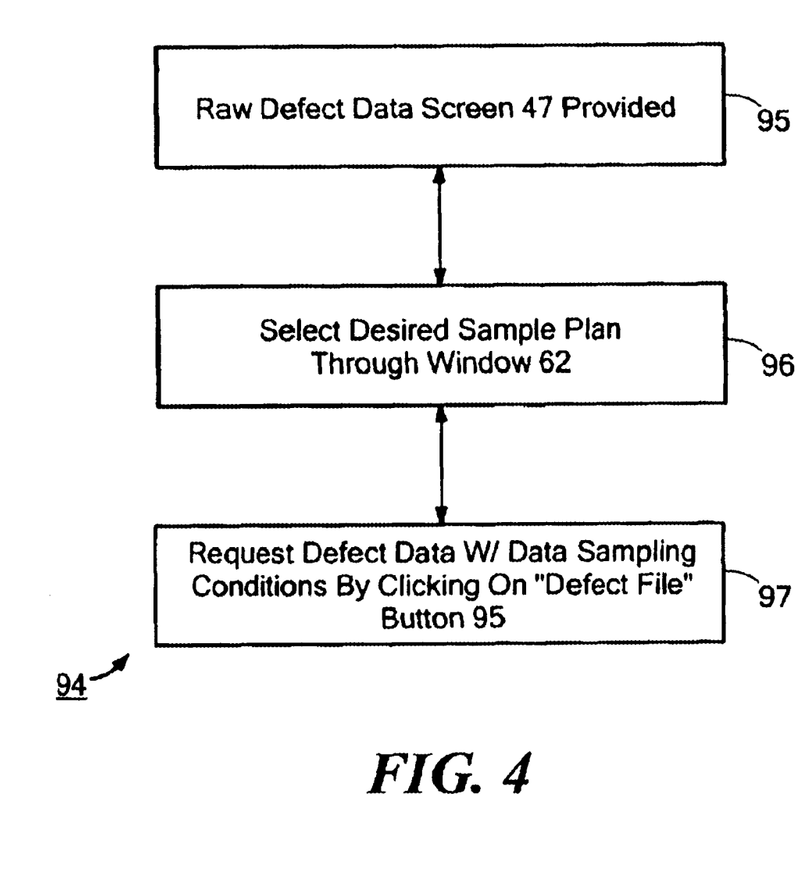
FIG. 4 is a partial flow chart detailing a sequence of steps which are executed to perform the run-time operation step shown in FIG. 2.

Referring now to FIG. 4, there is shown a flow chart detailing the process for performing the run time operation of extracting a defect data sample from database 19 using one of the defect sample plans, said process being identified by reference numeral 94.

In the first step of process 94, raw defect data screen 49 is provided, said step being represented by reference numeral 95 in FIG. 4. With raw defect data screen 49 provided as such, the user can provide defect sampling conditions in windows 51, 53, 55, 57, 61 and 69.

Having completed first step 95, the user selects a particular defect sample plan from screen 49, said step being represented by reference numeral 96 in FIG. 4. Specifically, the user selects a particular pre-established sample plan from within "Sample Plan" window 62. As can be appreciated, clicking on a particular sample plan implements the one or more defect sampling conditions associated with said sample plan during the defect data extraction step, as will be described further below.

Having established all of the desired defect sampling conditions in steps 95 and 96, the user performs the defect data sampling request using the one or more selected defect sampling conditions, said step being represented by reference numeral 97 in FIG. 4. Specifically, with the particular defect sampling conditions listed within the various windows of screen 49, the extraction of the defect data file from database 19 is accomplished by clicking on a "Get Defect File" button, which is represented by reference numeral 60 in FIG. 5.

In use, system 11 can be used in the following manner to review one or more layers of one or more semiconductor wafers for defects. As seen most clearly in the block diagram shown in FIG. 2, in the first step performed by system 11, inspection device 13 scans one layer of at least one semiconductor wafer for defects and then uploads the entire set of defect data for the at least one semiconductor wafer into central database 19, said step being identified generally in FIG. 2 by reference numeral 98.

Figure 2:
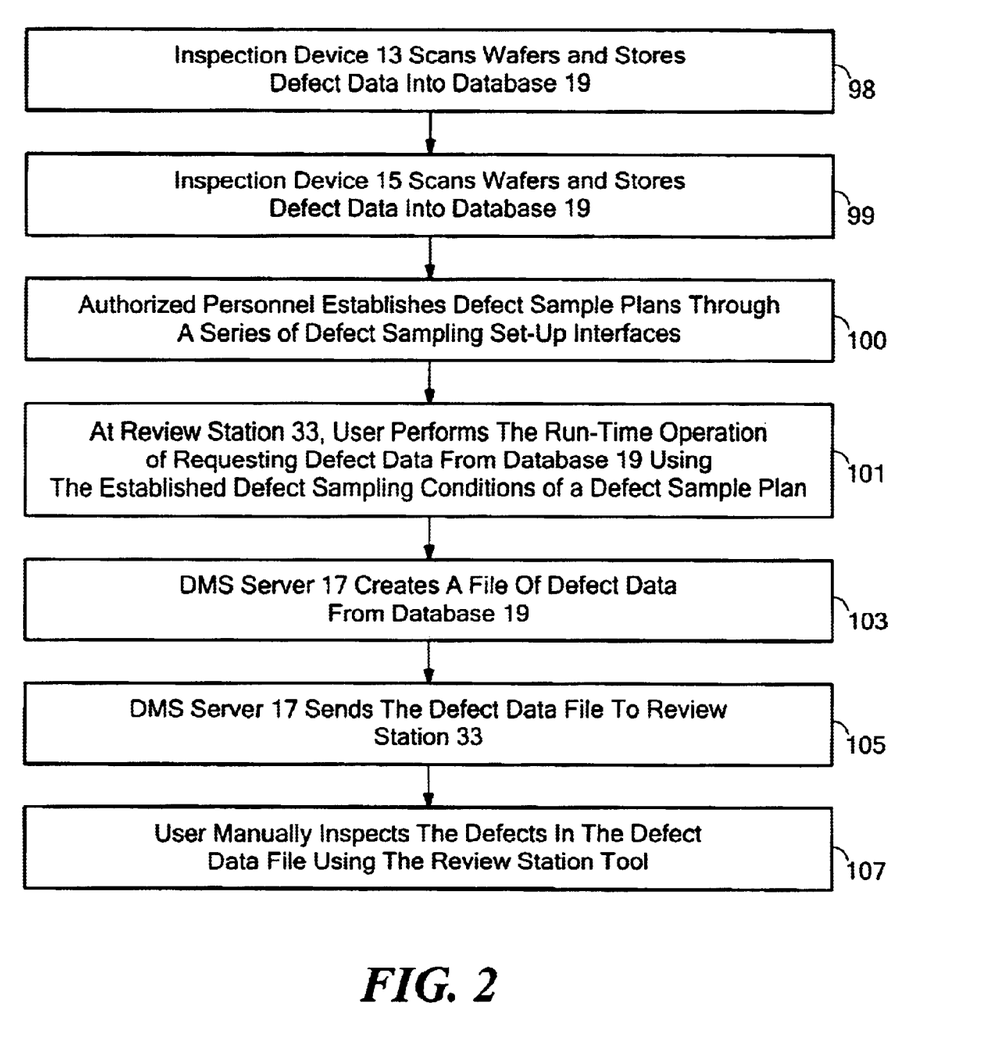
FIG. 2 is a partial flow chart detailing a method for reviewing at least one layer of at least one semiconductor wafer for defects using the data management system of FIG. 1.

In the second step performed by system 11, inspection device 15 scans another layer of at least one semiconductor wafer for defects and then uploads the entire set of defect data for the at least one semiconductor wafer into central database 19, said step being identified generally in FIG. 2 by reference numeral 99.

In the third step performed by system 11, an authorized person performs defect sample plan set-up process 45, thereby establishing the particular defect sampling conditions to be associated with each defect sample plans, said step being identified generally in FIG. 2 by reference numeral 100. It should be noted that, if the user has previously performed defect sample plan set-up process 45, step 100 can be skipped and the user can proceed directly to the fourth step.

In the fourth step performed by system 11, the user performs run-time operation 94, said step being identified generally in FIG. 2 as reference numeral 101. Specifically, in step 101, the user requests defect data stored in central database 19 using one or more defect sampling conditions.

In the fifth step performed by system 11, DMS server 17 responds to the request made by review station 33 by creating a file which contains the requested defect data, said step being identified generally in FIG. 2 by reference numeral 103. It should be noted that review station server software 39 converts said file from a database file format to a native file format for review station 33.

In the sixth step performed by system 11, DMS server 17 sends the file containing the requested defect data to review station 33, said step being identified generally in FIG. 2 by reference numeral 105.

In the final step performed by system 11, the user is able to visually inspect individual defects contained within the file, said step being identified generally in FIG. 2 by reference numeral 107. Specifically, the user utilizes a high magnification microscope, or other similar tool at review station 33, to further examine individual defects residing on the wafer surface which are contained within the file.

It should be noted that system 11 provides a number of notable advantages.

As a first advantage, because all of the raw historical defect data detected by inspection devices 13 and 15 are stored in central database 19, system 11 is able to sample defect data from multiple layers of multiple wafers. To the contrary, conventional systems typically review the defect data from only a single layer of a single wafer. As a result, system 11 is able to reduce production overhead and to increase manufacturing efficiency, which is highly desirable.

As a second advantage, a single system 11 is created which provides the software for DMS server 17 and review client software 37 for review station 33. To the contrary, conventional systems require the manufacturer of review station 33 to create software necessary to interface review station 33 with review station server software 39. Accordingly, because system 11 provides both the review station server software 39 for DMS server 17 and review client software 37 for review station 33, the process for synchronizing, testing and/or enhancing either piece of software is considerably simplified, which is highly desirable.

The embodiment shown of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A system for reviewing at least one layer of at least one semiconductor wafer for defects, said system being interfaced to a first inspection device which scans the at least one layer of the at least one semiconductor wafer for defects, said first inspection device producing a first set of detected defects from scanning the at least one layer of the at least one semiconductor wafer, said system being interfaced to a review station for reviewing the at least one layer of the at least one semiconductor wafer, said system comprising:
    (a) a server connected to said first inspection device and said review station, said server comprising a database into which said first set of detected defects is stored, and
    (b) review client software which interfaces with said review station, said review client software enabling a sample of said first set of detected defects to be extracted from the database using at least one defect sampling condition, said at least one defect sampling condition relating to a particular defect characteristic.

2. The system as claimed in claim 1 wherein said system is interfaced to a second inspection device which scans at least one layer of at least one semiconductor wafer for defects, said second inspection device producing a second set of detected defects from scanning the at least one layer of the at least one semiconductor wafer.

3. The system as claimed in claim 2 wherein said review client software enables a sample of said first and second sets of detected defects to be extracted from the database using at least one defect sampling condition, said at least one defect sampling condition relating to a particular defect characteristic.

4. The system as claimed in claim 3 wherein said review client software enables a sample of detected defects on multiple layers of the at least one semiconductor wafer to be extracted from the database using at least one defect sampling condition.

5. The system as claimed in claim 3 wherein said review client software enables a sample of detected defects on multiple semiconductor wafers to be extracted from the database using at least one defect sampling condition.

6. The system as claimed in claim 1 wherein said at least one defect sampling condition pertains to the size of one or more of said detected defects.

7. The system as claimed in claim 1 wherein said at least one defect sampling condition pertains to the density of one or more of said detected defects.

8. The system as claimed in claim 1 wherein said at least one defect sampling condition pertains to the class of one or more of said detected defects.

9. The system as claimed in claim 1 wherein said at least one defect sampling condition pertains to the test name of one or more of said detected defects.

10. The system as claimed in claim 1 wherein review station server software is installed onto said server and wherein said review client software is installed onto said review station.

11. The system as claimed in claim 10 wherein said review station server software and said review client software together enable said review station to directly interface with the database in said server.

12. The system as claimed in claim 11 wherein said review client software provides a sequence of graphical user interfaces to enable the sample of said first set of detected defects to be extracted from the database using at least one defect sampling condition.

13. The system as claimed in claim 1 further comprising a data analysis station connected to said server to perform data analysis functions of said first set of detected defects.

14. A method for reviewing at least one layer of at least one semiconductor wafer for defects using at least one inspection mechanism, said at least one inspection mechanism being connected to a server which includes a database, said server being connected to a review station, said method comprising the steps of:
    (a) scanning the at least one layer of the at least one semiconductor wafer using said at least one first inspection mechanism, said scanning step yielding a first set of detected defects,
    (b) storing said first set of detected defects into said database,
    (c) requesting a sample of said first set of detected defects using at least one defect sampling condition, said requesting step being performed at said review station,
    (d) extracting the sample of said first set of detected defects using at least one defect sampling condition from the database, said extracting step being performed by said server in response to said requesting step, and
    (e) sending the extract sample of said first set of detected defects from said server to said review station.

15. The method as claimed in 14 further comprising a set-up step for creating the at least one defect sampling condition.

16. The method as claimed in claim 15 wherein said set-up step is accomplished through a sequence of graphical user interfaces.

17. The method as claimed in claim 16 wherein the sequence of graphical user interfaces comprises:
   (a) a raw defect data screen for displaying the extracted sample of said first set of detected defects,
   (b) a sample plan setup dialog screen for displaying the at least one defect sampling condition, and
   (c) a defect sampling condition form screen for creating each of the at least one defect sampling condition.

18. The system as claimed in claim 14 wherein the at least one defect sampling condition used in said requesting step relates to a particular characteristic of each defect.

19. The method as claimed in claim 14 wherein the at least one defect sampling condition used in said requesting step relates to the detected defects which are present within a particular region of the at least one layer of the at least one semiconductor wafer.

20. The method as claimed in claim 14 wherein the at least one defect sampling condition used in said requesting step pertains to the size of one or more of said detected defects.

21. The method as claimed in claim 14 wherein the at least one defect sampling condition used in said requesting step pertains to the density of one or more of said detected defects.

22. The method as claimed in claim 14 wherein the at least one defect sampling condition used in said requesting step pertains to the class of one or more of said detected defects.

23. The method as claimed in claim 14 wherein the at least one defect sampling condition used in said requesting step pertains to the test name of one or more of said detected defects.

24. The method as claimed in claim 14 wherein said extracting step extracts from the database a sample of defects detected on multiple layers of the at least one semiconductor wafer using the at least one defect sampling condition.

25. The method as claimed in claim 14 wherein said extracting step extracts from the database a sample of defects detected on multiple semiconductor wafers using the at least one defect sampling condition.

26. A system for reviewing a layer of a semiconductor wafer for defects, said system being interfaced to a first inspection device which scans the layer of the semiconductor wafer for defects, said first inspection device producing a first set of detected defects from scanning the layer of the semiconductor wafer, said system being interfaced to a review station for reviewing the layer of the semiconductor wafer, said system comprising:
   (a) a server connected to said first inspection device and said review station, said server comprising a database into which said first set of detected defects is stored, and
   (b) review client software which interfaces with said review station, said review client software enabling a sample of said first set of detected defects to be extracted from the database using a sampling condition, the sample of said first set of detected defects to be extracted from the database including less than the entire first set of detected defects.

27. The system as claimed in claim 26 wherein said sampling condition relates to the detected defects which are present within a particular region of the layer of the semiconductor wafer.

28. A method for reviewing first and second layers of a semiconductor wafer for defects using at least one inspection mechanism, said at least one inspection mechanism being connected to a server which includes a database, said server being connected to a review station, said method comprising the steps of:
   (a) scanning the first layer of the semiconductor wafer using said at least one inspection mechanism, said scanning the first layer of the semiconductor wafer step yielding a first set of detected defects,
   (b) storing the first set of detected defects into said database,
   (c) scanning the second layer of the semiconductor wafer using said at least one inspection mechanism, said scanning the second layer of the semiconductor wafer step yielding a second set of detected defects,
   (d) storing the second set of detected defects into said database,
   (e) requesting a sample of the first and second sets of detected defects which are stored into the database, said sample being limited to the defects which are not common to both the first and second sets of detected defects, said requesting step being performed at said review station,
   (f) extracting said sample from the database, said extracting step being performed by said server in response to said requesting step, and
   (g) sending the extracted sample from said server to said review station.

* * * * *